US011151978B1

(12) United States Patent
Tseng et al.

(10) Patent No.: US 11,151,978 B1
(45) Date of Patent: Oct. 19, 2021

(54) SYSTEM AND METHOD FOR FAN NOISE CANCELLER

(71) Applicant: Dell Products L.P., Round Rock, TX (US)

(72) Inventors: Chun-Fa Tseng, Taipei (TW); Ming-Hui Pan, Taipei (TW); Jyh-Yinn Lin, Taipei (TW); Hung-Wen Wu, New Taipei (TW)

(73) Assignee: Dell Products L.P., Round Rock, TX (US)

( * ) Notice: Subject to any disclaimer, the term of this patent is extended or adjusted under 35 U.S.C. 154(b) by 0 days.

(21) Appl. No.: 16/952,714

(22) Filed: Nov. 19, 2020

(51) Int. Cl.
*A61F 11/06* (2006.01)
*G10K 11/178* (2006.01)
*F04D 29/66* (2006.01)

(52) U.S. Cl.
CPC ...... *G10K 11/17857* (2018.01); *F04D 29/665* (2013.01); *G10K 2210/108* (2013.01); *G10K 2210/109* (2013.01); *G10K 2210/11* (2013.01)

(58) Field of Classification Search
CPC ....... G10K 11/17857; G10K 2210/108; G10K 2210/109; G10K 2210/11; F04D 29/665
USPC .............................................. 381/71.1, 71.13
See application file for complete search history.

(56) References Cited

U.S. PATENT DOCUMENTS 5,508,477 A * 4/1996 Kato .................... G10K 11/172
181/205

* cited by examiner

*Primary Examiner* — Ammar T Hamid
(74) *Attorney, Agent, or Firm* — Baker Botts L.L.P.

(57) ABSTRACT

A fan noise cancellation device comprises a base with a resonant ring formed with a plurality of resonance channels and a cover coupled to the base. Each resonance channel comprises an inner channel and an outer channel. Each inner channel has an opening to the resonant ring and has a length corresponding to a frequency. A baffle positioned in each inner channel determines an effective length of the inner channel. The inner channel baffles are coupled to the cover, wherein rotation of the cover relative to the resonance ring changes the position of the inner channel baffles to change the effective lengths of the inner channels to adjust the fan noise cancellation waveform frequency. Vanes on the cover are positioned in an airflow such that the airflow rotates the cover, and a spring in each resonance channel counteracts the rotation to adjust the inner channels.

17 Claims, 6 Drawing Sheets

SYSTEM AND METHOD FOR FAN NOISE CANCELLER

BACKGROUND

Field of the Disclosure

This disclosure relates generally to information handling systems and, more particularly, to systems for cancelling noise associated with a fan generating an airflow in an information handling system.

Description of the Related Art

As the value and use of information continues to increase, individuals and businesses seek additional ways to process and store information. One option available to users is information handling systems. An information handling system generally processes, compiles, stores, and/or communicates information or data for business, personal, or other purposes thereby allowing users to take advantage of the value of the information. Because technology and information handling needs and requirements vary between different users or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific user or specific use such as financial transaction processing, airline reservations, enterprise data storage, or global communications. In addition, information handling systems may include a variety of hardware and software components that may be configured to process, store, and communicate information and may include one or more computer systems, data storage systems, and networking systems.

A fan in an information handling system operates at various speeds to remove heat generated by components. Typically, as the fan speed increases, the fan generates more noise. The noise may be attributed to blade passing tone, particularly when fan blades pass between small gaps between the fan rotor and stationary objects.

SUMMARY

Embodiments disclosed herein may be generally directed to information handling systems and systems for cancelling noise generated by fans operating in the information handling systems.

In one respect, embodiments may be directed to a fan noise cancellation device for generating a fan noise cancellation waveform at a plurality of points. A fan noise cancellation device may comprise a base comprising a resonance ring and a plurality of resonance channels. Each resonance channel may be formed from an inner channel arranged around the resonance ring and an outer channel arranged outward of the inner channel. Each inner channel of the plurality of inner channels comprises an opening to the resonance ring. A cover may be coupled to the base such that air can enter or exit each inner channel only through the opening to the resonance ring and each resonance channel is configured to generate a fan noise cancellation waveform at a corresponding opening based on an airflow passing through the fan noise cancellation device. The fan noise cancellation waveform has a frequency based on a length of a corresponding inner channel of a resonance channel.

In some embodiments, the cover comprises a plurality of inner channel baffles and a plurality of outer channel baffles to adjust the noise cancellation waveform frequency. Each inner channel baffle is positioned in an inner channel of a respective resonance channel of the plurality of resonance channels. An angular position of an inner channel baffle in an inner channel determines an effective length of the inner channel. Each resonance channel generates the fan noise cancellation waveform at a frequency based on the effective length of a respective inner channel. Rotation of the cover relative to the base changes the angular position of the plurality of inner channel baffles in the plurality of inner channels. In some embodiments, the cover comprises a plurality of vanes, wherein airflow in contact with the plurality of vanes causes rotation of the cover relative to the base to change the angular position of the plurality of inner channel baffles in the plurality of inner channels. In some embodiments, each outer channel of the plurality of outer channels contains a spring and an outer channel baffle. Rotation of the cover to reduce the effective length of an inner channel contacts an outer channel baffle with a spring, wherein each spring in the plurality of springs is configured to resist rotation of the cover or bias the cover in a direction to increase the effective length of each inner channel.

The fan noise cancellation device may be coupled to a fan configured to operate over a range of operating speeds, wherein each operating speed is associated with an airflow volume and a waveform frequency. One or more of the plurality of vanes, the plurality of springs, the overall length of each inner channel of the plurality of inner channels may be configured to cause the plurality of resonance channels to generate the fan noise cancellation waveform over the range of operating speeds. The range of operating speeds may correspond to a range of frequencies associated with a performance drop of a component in an information handling system. Each resonance channel of the plurality of resonance channels may have a length configured to generate a fan noise cancellation waveform corresponding to a blade passing tone (BPT).

A chassis for an information handling system may include a plurality of components, a fan for generating an airflow to cool the plurality of components, the fan also generating a fan noise waveform based on the airflow, and a fan noise cancellation device for generating a fan noise cancellation waveform at a plurality of points. A fan noise cancellation device may comprise a base comprising a resonance ring and a plurality of resonance channels. Each resonance channel may be formed from an inner channel arranged around the resonance ring and an outer channel arranged outward of the inner channel, wherein each inner channel of the plurality of inner channels comprises an opening in the resonance ring. A cover may be coupled to the base, wherein each resonance channel of the plurality of resonance channels is configured to generate a fan noise cancellation waveform at a corresponding opening based on an airflow passing through the fan noise cancellation device, and the fan noise cancellation waveform has a frequency based on a length of a corresponding inner channel.

One or more of the effective length of each inner channel, the opening in each inner channel, and the spring in each outer channel may be configured to cause the plurality of resonance channels to generate the fan noise cancellation waveform over a frequency range. The frequency range may correspond to a frequency associated with a performance drop of a component in the information handling system.

Each resonance channel of the plurality of resonance channels may have a length configured to generate a fan noise cancellation waveform corresponding to a blade passing tone (BPT).

A method of manufacturing a fan noise cancellation device for generating a fan noise cancellation waveform at a plurality of points may comprise forming a base comprising a resonance ring for allowing airflow to pass through the fan noise cancellation device; forming a plurality of inner channels around the resonance ring, wherein each inner channel is formed with a length corresponding to a fan noise cancellation waveform frequency; forming a plurality of openings on an inner surface of the resonance ring, wherein each inner channel of the plurality of inner channels is in fluid communication with the resonance ring via an opening of the plurality of openings, and coupling a cover to the base, wherein airflow through the resonance ring causes the plurality of resonance channels to generate a fan noise cancellation waveform at the fan noise cancellation waveform frequency. Forming the plurality of inner channels around the resonance ring may include forming each inner channel with a length corresponding to a blade passing tone (BPT). Coupling the cover to the base may comprise positioning an inner channel baffle in each inner channel of the plurality of inner channels such that an angular position of the inner channel baffle determines an effective length of the inner channel. The cover may be rotatably coupled to the base, wherein rotating the cover relative to the base changes the angular position of the inner channel baffle in the inner channel to change the effective length of the inner channel.

The method may include forming a plurality of outer channels around the plurality of inner channels, positioning a plurality of springs in the plurality of outer channels, forming a plurality of outer channel baffles on the cover, and forming a plurality of vanes on the cover to generate a rotation force when in contact with an airflow. The cover may be rotatably coupled to the base, wherein each inner channel baffle is positioned in an inner channel of the plurality of inner channels such that an angular position of the inner channel baffle determines an effective length of the inner channel. Each outer channel baffle may be positioned in an outer channel of the plurality of outer channels and may be configured for contact with a spring of the plurality of springs.

Airflow in contact with the plurality of vanes generates a first rotation force to rotate the cover relative to the base in a first direction to change the angular position of the plurality of inner channel baffles to decrease the effective length of each inner channel. Contact between the plurality of outer channel baffles with the plurality of springs generates a second rotation force opposite the first rotation force to rotate the cover relative to the base in a second direction to change the angular position of the plurality of inner channel baffles to increase the effective length of each inner channel.

BRIEF DESCRIPTION OF THE DRAWINGS

For a more complete understanding of the invention and its features and advantages, reference is now made to the following description, taken in conjunction with the accompanying drawings, in which.

DESCRIPTION OF PARTICULAR EMBODIMENT(S)

In the following description, details are set forth by way of example to facilitate discussion of the disclosed subject matter. It should be apparent to a person of ordinary skill in the field, however, that the disclosed embodiments are exemplary and not exhaustive of all possible embodiments.

For the purposes of this disclosure, an information handling system may include an instrumentality or aggregate of instrumentalities operable to compute, classify, process, transmit, receive, retrieve, originate, switch, store, display, manifest, detect, record, reproduce, handle, or utilize various forms of information, intelligence, or data for business, scientific, control, entertainment, or other purposes. For example, an information handling system may be a personal computer, a consumer electronic device, a network storage device, or another suitable device and may vary in size, shape, performance, functionality, and price. The information handling system may include memory, one or more processing resources such as a central processing unit (CPU) or hardware or software control logic. Additional components of the information handling system may include one or more storage devices, one or more communications ports for communicating with external devices as well as various input and output (I/O) devices, such as a keyboard, a mouse, and one or more video displays. The information handling system may also include one or more buses operable to transmit communication between the various hardware components.

Embodiments disclosed herein are described with respect to fans associated with cooling CPUs, HDDs and other high power components. Particular embodiments are best understood by reference to FIGS. 1-6, wherein like numbers are used to indicate like and corresponding parts.

Figure 1:
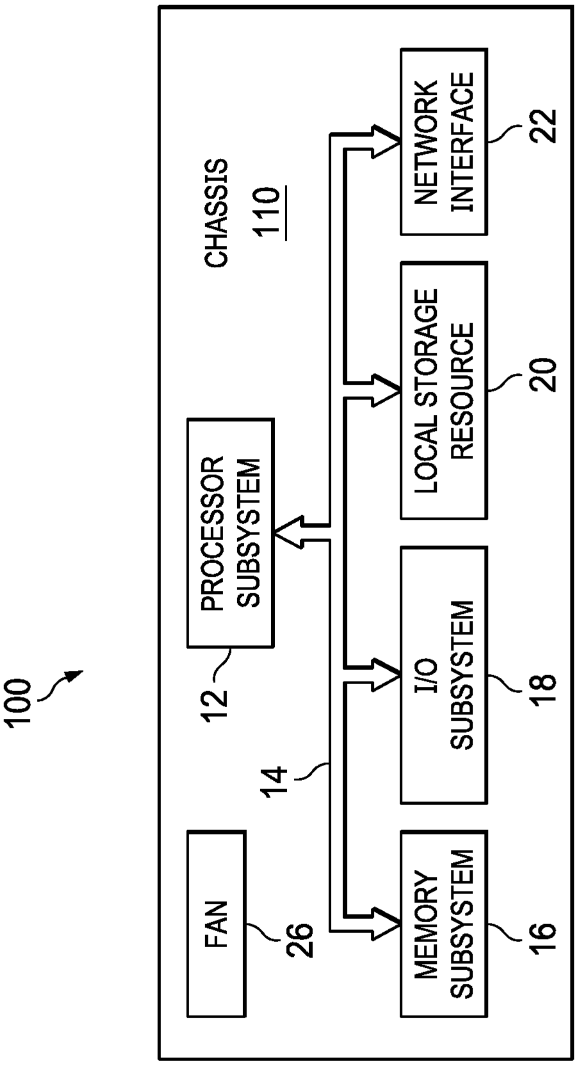
FIG. 1 is a block diagram of selected elements of an embodiment of an information handling system.

Turning to the drawings, FIG. 1 illustrates a block diagram depicting selected elements of an embodiment of information handling system 100 in chassis 110. It is noted that FIG. 1 is not drawn to scale but is a schematic illustration.

As shown in FIG. 1, components of information handling system 100 may include, but are not limited to, a processor subsystem 12, which may comprise one or more processors, and a system bus 14 that communicatively couples various system components to processor subsystem 12 including, for example, a memory subsystem 16, an I/O subsystem 18, local storage resource 20, and network interface 22. Chassis 110 may further include fan 26 for cooling components in chassis 110.

Processor subsystem 12 may comprise a system, device, or apparatus operable to interpret and execute program instructions and process data, and may include a microprocessor, microcontroller, digital signal processor (DSP), application specific integrated circuit (ASIC), or another digital or analog circuitry configured to interpret and execute program instructions and process data. In some embodiments, processor subsystem 12 may interpret and execute program instructions and process data stored locally (e.g., in memory subsystem 16). In the same or alternative embodiments, processor subsystem 12 may interpret and execute program instructions and process data stored remotely (e.g., in a network storage resource).

System bus 14 may refer to a variety of suitable types of bus structures, e.g., a memory bus, a peripheral bus, or a local bus using various bus architectures in selected embodiments. For example, such architectures may include, but are not limited to, Micro Channel Architecture (MCA) bus, Industry Standard Architecture (ISA) bus, Enhanced ISA (EISA) bus, Peripheral Component Interconnect (PCI) bus, PCI-Express bus, HyperTransport (HT) bus, and Video Electronics Standards Association (VESA) local bus.

Memory subsystem 16 may comprise a system, device, or apparatus operable to retain and retrieve program instructions and data for a period of time (e.g., computer-readable media). Memory subsystem 16 may comprise random access memory (RAM), electrically erasable programmable read-only memory (EEPROM), a PCMCIA card, flash memory, magnetic storage, opto-magnetic storage, and/or a suitable selection and/or array of volatile or non-volatile memory that retains data after power to its associated information handling system, such as system 100, is powered down.

In information handling system 100, I/O subsystem 18 may comprise a system, device, or apparatus generally operable to receive and transmit data to or from or within information handling system 100. I/O subsystem 18 may represent, for example, a variety of communication interfaces, graphics interfaces, video interfaces, user input interfaces, and peripheral interfaces. In various embodiments, I/O subsystem 18 may be used to support various peripheral devices, such as a touch panel, a display adapter, a keyboard, a touch pad, or a camera, among other examples. In some implementations, I/O subsystem 18 may support so-called 'plug and play' connectivity to external devices, in which the external devices may be added or removed while information handling system 100 is operating.

Local storage resource 20 may comprise computer-readable media (e.g., hard disk drive, floppy disk drive, CD-ROM, and other type of rotating storage media, flash memory, EEPROM, or another type of solid-state storage media) and may be generally operable to store instructions and data.

Network interface 22 may be a suitable system, apparatus, or device operable to serve as an interface between information handling system 100 and a network (not shown). Network interface 22 may enable information handling system 100 to communicate over a network using a suitable transmission protocol or standard. In some embodiments, network interface 22 may be communicatively coupled via a network to a network storage resource (not shown). A network coupled to network interface 22 may be implemented as, or may be a part of, a storage area network (SAN), personal area network (PAN), local area network (LAN), a metropolitan area network (MAN), a wide area network (WAN), a wireless local area network (WLAN), a virtual private network (VPN), an intranet, the Internet or another appropriate architecture or system that facilitates the communication of signals, data and messages (generally referred to as data). A network coupled to network interface 22 may transmit data using a desired storage or communication protocol, including, but not limited to, Fibre Channel, Frame Relay, Asynchronous Transfer Mode (ATM), Internet protocol (IP), other packet-based protocol, small computer system interface (SCSI), Internet SCSI (iSCSI), Serial Attached SCSI (SAS) or another transport that operates with the SCSI protocol, advanced technology attachment (ATA), serial ATA (SATA), advanced technology attachment packet interface (ATAPI), serial storage architecture (SSA), integrated drive electronics (IDE), or any combination thereof. A network coupled to network interface 22 or various components associated therewith may be implemented using hardware, software, or any combination thereof.

Fan Noise Affects Operation of Components

Fan 26 may be used to remove heat from components in information handling system 110 by generating an airflow through chassis 110. As fan 26 rotates, it generates a fan noise waveform. Generally, a higher fan speed generally results in more fan noise. However, fan noise is typically highest at a particular frequency referred to as blade passing tone (BPT, also referred to as blade passing frequency or BPF) or over a range of frequencies including the BPT. At the BPT, fan noise may affect operation of a component in information handling system 100.

Figure 2:
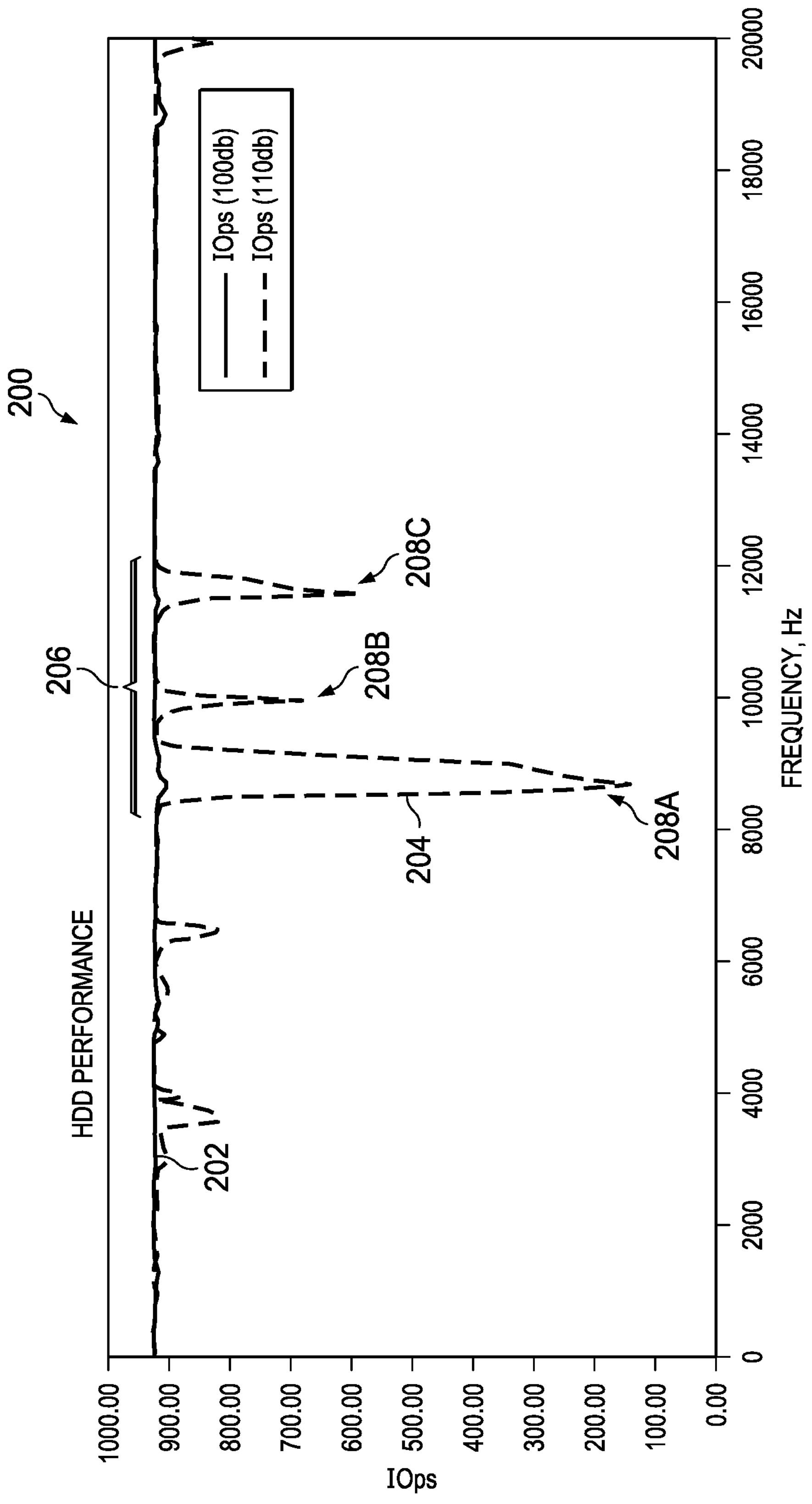
FIGS. 2 and 3 depict performance graphs for an exemplary hard disk drive (HDD), illustrating possible effects of fan noise on the performance of components in an information handling system.
Figure 3:
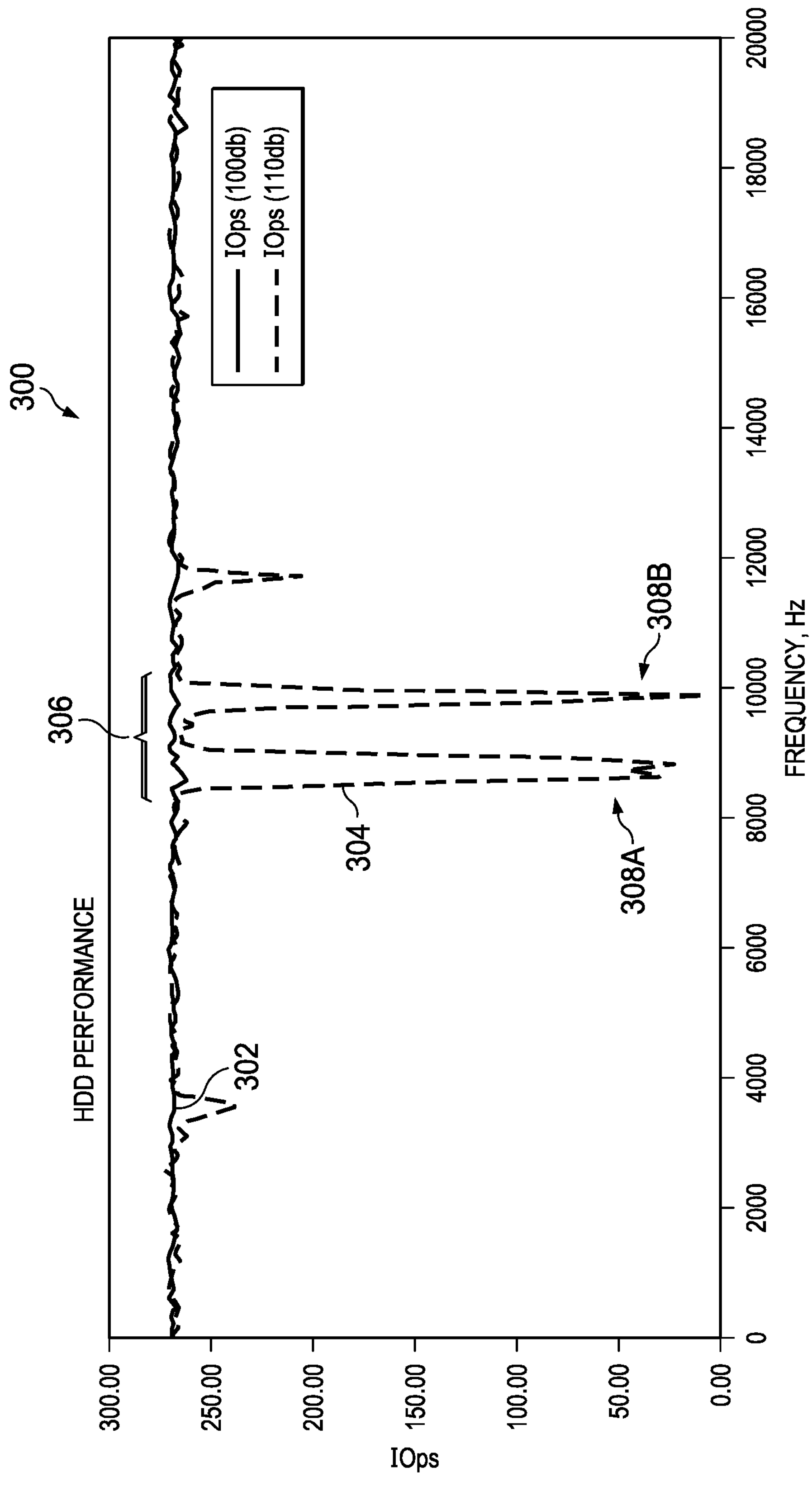

By way of example, FIGS. 2 and 3 depict graphs 300 and 200 of exemplary performance levels for a hard disk drive (HDD), illustrating possible effects of fan noise on performance levels of components. As depicted in FIGS. 2 and 3, a hard drive (HDD) may be capable of high Input/Output operations per second (IOps) but may reduce its IOps performance if it is subjected to or detects a frequency (e.g., 9 k Hz) or a range of frequencies (e.g., 8 k-12 k Hz) in chassis 110.

As depicted in FIG. 2, for the exemplary HDD operating in a first read/write mode, line 202 corresponding with the HDD operating in the presence of a 100 dB noise indicates the HDD may be capable of performing at over 900 IOps over all frequencies. However, line 204 corresponding to the HDD performing in the presence of a 110 dB noise indicates the HDD may reduce its performance over frequency range 206. As depicted in FIG. 2, frequency range 206 may be from approximately 8 k Hz to 12 k Hz. Frequency range 206 may be include one or more performance drops. For example, performance drop 208A indicates the HDD may reduce its IOps performance to less than 200 IOps at a frequency near 9 k Hz, performance drop 208B indicates the HDD may reduce its IOps performance to less than 700 IOps in the presence at a frequency near 10 k Hz and performance drop 208C indicates the HDD may reduce its performance to less than 600 IOps in the presence at a frequency near 12 k Hz.

As depicted in FIG. 3, for the exemplary HDD operating in a second read/write mode, line 302 corresponding with the HDD operating in the presence of a 100 dB noise indicates the HDD may be capable of performing at over 250 IOps over all frequencies. However, line 304 corresponding to the HDD performing in the presence of a 110 dB noise indicates the HDD may reduce its IOps performance over frequency range 306. As depicted in FIG. 3, frequency range 306 may be from approximately 8 k Hz to 10 k Hz. Frequency range 306 may be include one or more performance drops. For example, performance drop 308A indicates the HDD may reduce its IOps performance to less than 50 IOps at a frequency near 9 k Hz and performance drop 308B indicates the HDD may reduce its IOps performance to almost 0 IOps in the presence of a frequency near 10 k Hz.

To overcome these deficiencies, embodiments disclosed herein comprise a fan noise cancellation device to reduce fan noise in chassis 110 to allow fan 26 to operate at high speeds to efficiently cool components in information handling system 100 and allow components to operate at higher performance levels. A fan noise cancellation device may generate a fan noise cancellation waveform at multiple sources to reduce fan noise or mitigate the effects of fan noise on component performance levels.

Figure 4:
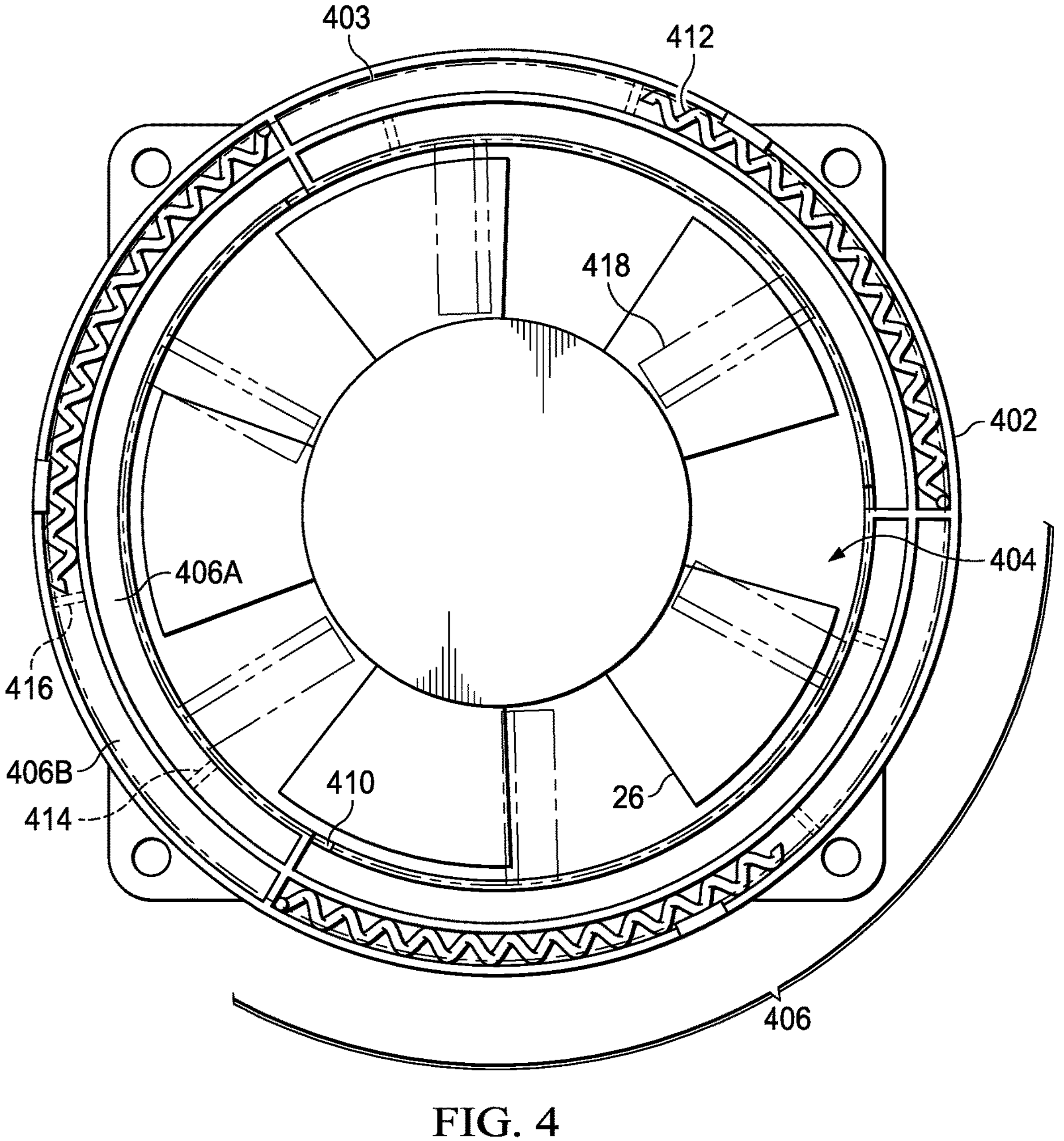
FIG. 4 is a top view of one embodiment of a fan noise cancellation device for cancelling fan noise in an information handling system.
Figure 5:
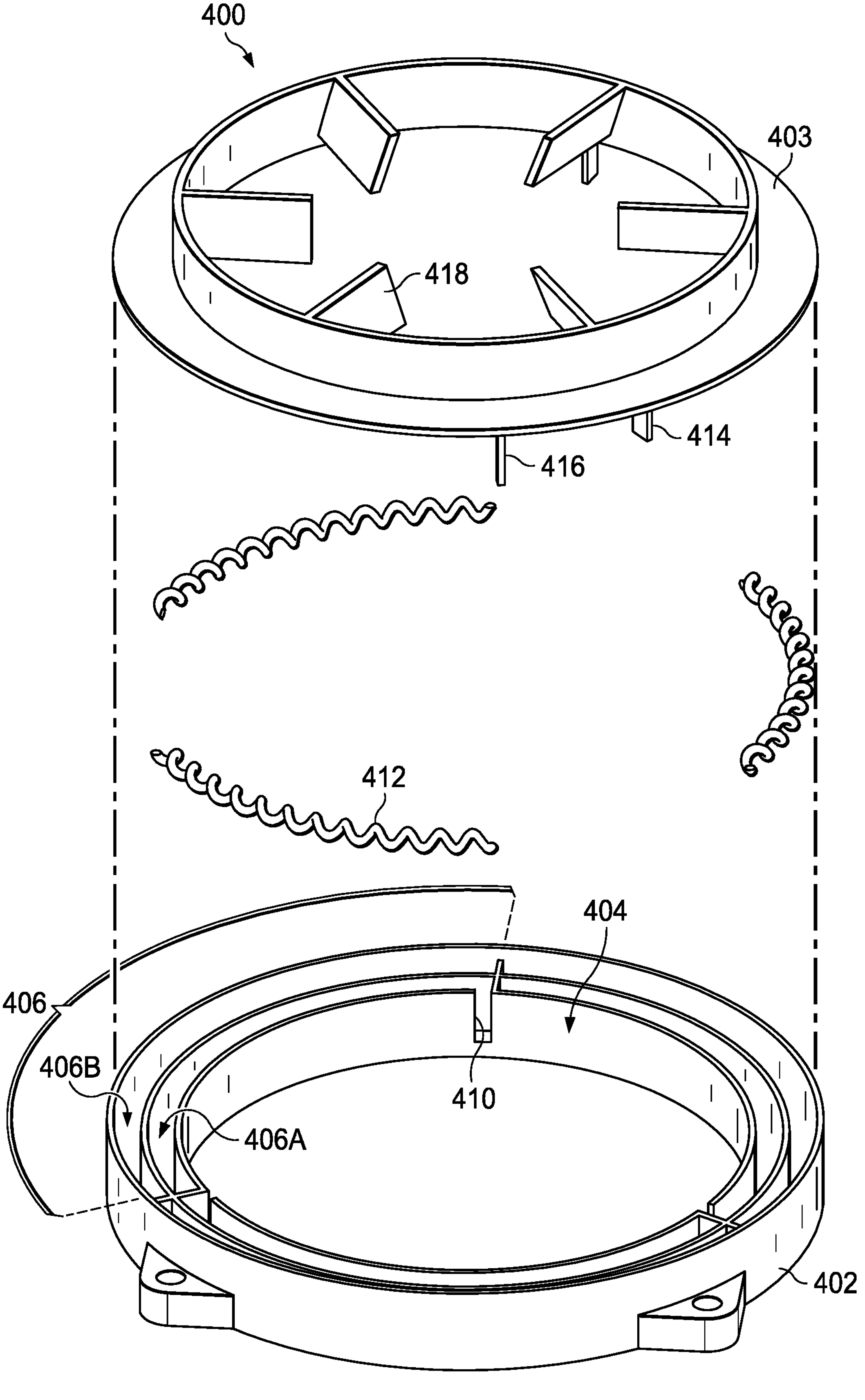
FIG. 5 is a perspective exploded view of one embodiment of a fan noise cancellation device for cancelling fan noise in an information handling system.
Figure 6:
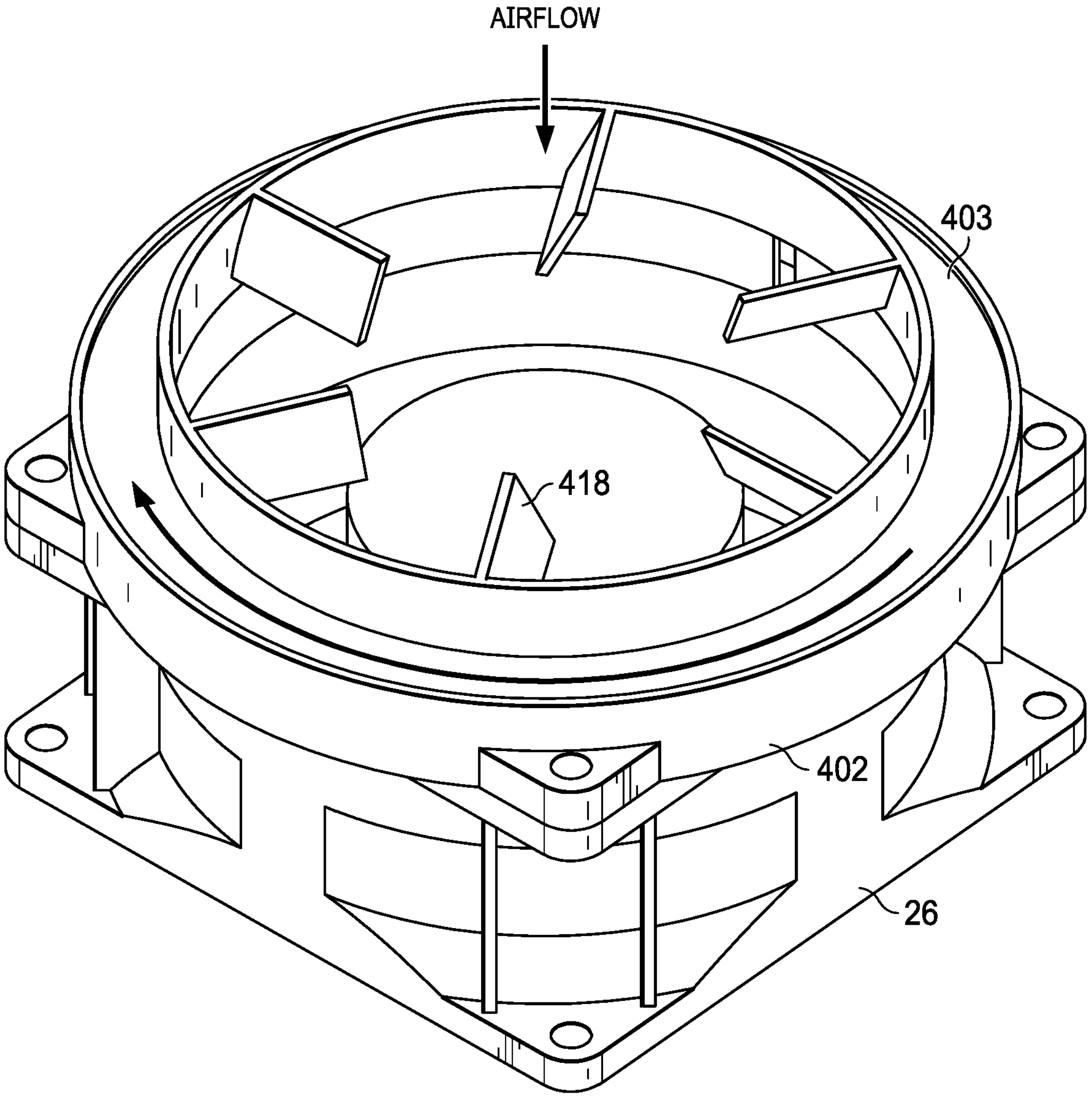
FIG. 6 is a perspective view of a fan and one embodiment of a fan noise cancellation device coupled to the fan for cancelling fan noise generated by the fan.

Referring to FIGS. 4-6, fan noise cancellation device 400 may comprise base 402 and cover 403 for positioning on and rotatably coupling to base 402.

Base 402 may be formed with resonance ring 404 through which airflow generated by fan 26 flows. Resonance ring 404 is surrounded by a plurality of resonance channels 406. Each resonance channel 406 in base 402 may be configured with inner channel 406A and outer channel 406B. Each inner channel 406A may be in fluid connection with resonance ring 404 via opening 410, whereby airflow through resonance ring 404 may enter inner channels 406A via openings 410. Each outer channel 406B may comprise spring 412, discussed below in greater detail.

Cover 403 may be coupled to base 402. In some embodiments, a bottom surface (not shown) of cover 403 effectively seals resonance channels 406 such that airflow enters and exits inner channels 406A only through openings 410 and springs 412 are constrained within outer channels 406B. In some embodiments, cover 403 may be rotatably coupled to base 402, and may comprise a plurality of vanes 418 for rotating cover 403 relative to base 402, discussed below in greater detail.

Airflow is Used to Generate a Fan Noise Cancelling Waveform

Referring to FIGS. 1-6, during operation of information handling system 100, fan 26 rotates to generate an airflow through chassis 110 and subsequently generates fan noise in the form of a fan noise waveform with a fan noise frequency. Fan noise cancellation device 400 may be configured to use the airflow generated by fan 26 to generate a fan noise cancellation waveform to cancel the fan noise waveform. Airflow may generate a noise cancellation waveform across multiple openings 410. Each opening 410 may be shaped to generate a noise cancellation waveform while minimizing drag, turbulence or other unwanted effects on airflow passing through resonance ring 404.

A fan noise cancellation waveform generated by fan noise cancellation device 400 depends on a length of each inner channel 406A. The length of each inner channel 406A determines the lowest frequency of a fan noise cancellation waveform that inner channel 406A can generate, wherein a longer length of each inner channel 406A results in a longer wavelength corresponding to a lower frequency fan noise cancellation waveform generated by each resonance channel 406. The number of resonance channels 406 may be determined by the length of each inner channel 406A, which may depend on a frequency of a noise cancellation waveform and the inner radius of resonance ring 404. For example, for resonance channels 406 having an overall length of approximately 87 mm and the inner radius of resonance ring 404 being 40 mm, fan noise cancellation device 400 may be formed with three resonance channels 406 with each inner channel 406A generating a fan noise cancellation waveform based on an inner channel length of 87 mm to cancel fan noise generated by fan 26 that generated the airflow.

Inner Channels have Adjustable Effective Lengths

Fan 26 may operate over a range of fan speeds and therefore generate a fan noise waveform over a range of frequencies. Embodiments may be configured with each inner channel 406A of resonance channels 406 having an effective length that can be adjusted to generate a fan noise cancellation waveform over a range of frequencies.

Referring still to FIGS. 4-6, in some embodiments, cover 403 comprises a plurality of inner channel baffles 414 for positioning in inner channels 406A, wherein an angular position of inner channel baffles 414 in inner channels 406A may define the effective length for each inner channel 406A. For the example above, the overall length of each inner channel 406A may be 87 mm but the angular position of inner channel baffles 414 in inner channels 406A may be adjusted such that the effective length of each inner channel 406A is less than 87 mm. Cover 403 may be rotatably coupled to base 402, wherein rotation of cover 403 relative to base 402 changes the angular position of inner channel baffles 414 in inner channels 406A to change the effective length of inner channels 406A. Rotation of cover 403 in a first direction relative to base 402 may be limited by outer channel baffles 416 contacting springs 412 positioned in outer channels 406B, discussed in greater detail below.

Automatic Adjustment of the Effective Length of the Inner Channels

Fan 26 may operate over a range of fan speeds depending on the cooling needs of components in chassis 110. Embodiments disclosed herein may be configured to automatically adjust an effective length of each inner channel 406A to generate a fan noise cancellation waveform with a frequency in a range of frequencies that could negatively affect the performance of a component in chassis 110. Referring to FIGS. 4-6, fan noise cancellation device 400 may be configured with cover 403 rotatably coupled to base 402, a set of inner channel baffles 414 positioned in inner channels 406A, a set of outer channel baffles 416 positioned in outer channels 406B, a plurality of vanes 418 coupled to cover 403 and a plurality of springs 412 in outer channels 406B.

Inner channel baffles 414 may be in a first angular position (e.g., at an end of inner channels 406A opposite openings 410) such that the effective length of each inner channel 406A is approximately equal to the total length of inner channel 406A to cause fan noise cancellation device 400 to generate a fan noise cancellation waveform at a first frequency (e.g., 8 k Hz). Airflow through resonance ring 404 contacts vanes 418 to cause vanes 418 to rotate cover 403 relative to base 402. Rotation of cover 403 changes the angular position of inner channel baffles 414 in inner channels 406A to a second angular position such that the effective length of each inner channel 406A of the plurality of inner channels 406A is reduced. As a result, the airflow over openings 410 generates a fan noise cancellation waveform at a second frequency higher (e.g., 9 k Hz) than the first frequency. Springs 412 positioned in outer channels 406B may resist rotation of cover 403, wherein a force generated by springs 412 may bias cover 403 in an opposite direction to increase the effective length of each inner channel 406A of the plurality of inner channels 406A. In some embodiments, the force generated by airflow contacting vanes 418 and the force generated by deflected springs 412 may be balanced such that the angular position of inner channel baffles 414 in inner channels 406A is substantially constant. Thus, if the fan speed increases, the force generated by the airflow on vanes 418 may be greater than the force generated by deflected springs 412 such that contact between the airflow and vanes 418 may bias cover 403 in a direction to shorten the effective length of each inner channel 406A of the plurality of inner channels 406A to increase the fan noise cancellation waveform frequency. Conversely, if the fan speed decreases, the force generated by the airflow on vanes 418 may be less than the force generated by deflected springs 412 such that springs 412 may bias cover 403 in a direction to increase the effective length of each inner channel 406A of the plurality of inner channels 406A to decrease the fan noise cancellation waveform frequency.

Fan Noise Cancellation Device Positioned Near Acoustic Noise Source

Embodiments of fan noise cancellation device 400 may be positioned in chassis 110 to generate a fan noise cancellation frequency as near to fan 26 as possible to reduce the possible effects of fan noise generated by fan 26. As depicted in FIG. 6, fan noise cancellation device 400 may be directly coupled to fan 26. In some embodiments, fan noise cancellation device 400 may be positioned in the airflow generated by fan 26 but not directly coupled to fan 26. Embodiments disclosed herein may be positioned proximate to fan 26 to reduce fan noise throughout chassis 110, which may allow fan 26 to be positioned closer than otherwise possible to components that could be affected by noise from fan 26. Furthermore, fan 26 with fan noise cancellation device 300 may be positioned upstream or downstream of other components.

Advantageously, embodiments disclosed herein may generate a fan noise cancellation waveform that reduces, offsets or otherwise mitigates the effects that fan noise can have on components in chassis 110 and allows for automatic adjustment of the fan noise cancellation waveform to accommodate variations in fan speed and other factors. The plurality of openings 410 also ensures the fan noise cancellation waveform is generated at multiple points in resonance ring 404 instead of a single point, which may be more effective at cancelling a fan noise waveform.

The above disclosed subject matter is to be considered illustrative, and not restrictive, and the appended claims are intended to cover all such modifications, enhancements, and other embodiments which fall within the true spirit and scope of the disclosure. Thus, to the maximum extent allowed by law, the scope of the disclosure is to be determined by the broadest permissible interpretation of the following claims and their equivalents, and shall not be restricted or limited by the foregoing detailed description.

What is claimed is:

1. A fan noise cancellation device comprising:
a base comprising:
a resonance ring; and
a plurality of resonance channels formed from a plurality of inner channels arranged around the resonance ring and a plurality of outer channels arranged around the plurality of inner channels, wherein each inner channel of the plurality of inner channels comprises an opening in the resonance ring; and
a cover coupled to the base, wherein
each inner channel of the plurality of inner channels is configured to generate a fan noise cancellation waveform at a corresponding opening based on an airflow passing through the fan noise cancellation device, and
the fan noise cancellation waveform has a frequency based on a length of a corresponding inner channel.

2. The fan noise cancellation device of claim 1, wherein:
the cover comprises a plurality of inner channel baffles and a plurality of outer channel baffles;
each inner channel baffle is positioned in an inner channel of the plurality of inner channels;
an angular position of the inner channel baffle in the inner channel determines an effective length of the inner channel;
the plurality of inner channels generate the fan noise cancellation waveform at a frequency based on the effective length of each inner channel; and
rotation of the cover relative to the base changes the angular position of the plurality of inner channel baffles in the plurality of inner channels to change the effective length of each inner channel.

3. The fan noise cancellation device of claim 1, wherein:
the cover comprises a plurality of vanes, wherein airflow in contact with the plurality of vanes causes rotation of the cover relative to the base to change the angular position of the plurality of inner channel baffles in the plurality of inner channels; and
each outer channel of the plurality of outer channels comprises a spring, wherein each spring in the plurality of springs is configured to resist rotation of the cover.

4. The fan noise cancellation device of claim 3, wherein:
the fan noise cancellation device is coupled to a fan configured to operate over a range of operating speeds, wherein each operating speed is associated with an airflow volume and a waveform frequency; and
one or more of the plurality of vanes, the plurality of springs, the overall length of each inner channel of the plurality of inner channels is configured to cause the plurality of inner channels to generate the fan noise cancellation waveform over the range of operating speeds.

5. The fan noise cancellation device of claim 4, wherein the range of operating speeds corresponds to a range of frequencies associated with a performance drop of a component in an information handling system.

6. The fan noise cancellation device of claim 1, wherein each inner channel comprises a length configured to generate a fan noise cancellation waveform corresponding to a blade passing tone (BPT).

7. A chassis for an information handling system, the chassis comprising:
a plurality of components;
a fan for generating an airflow to cool the plurality of components, the fan generating a fan noise waveform; and
a fan noise cancellation device comprising:
a base comprising:
a resonance ring; and
a plurality of resonance channels formed from a plurality of inner channels arranged around the resonance ring and a plurality of outer channels arranged around the plurality of inner channels, wherein each inner channel of the plurality of inner channels comprises an opening in the resonance ring; and
a cover coupled to the base, wherein airflow through the resonance ring causes the plurality of inner channels to generate a fan noise cancellation waveform at the opening in each inner channel, wherein the fan noise cancellation waveform has a frequency based on a length of each inner channel.

8. The chassis of claim 7, wherein:
the cover comprises a plurality of inner channel baffles and a plurality of outer channel baffles;
each inner channel baffle is positioned in an inner channel of a resonance channel of the plurality of resonance channels;
an angular position of the inner channel baffle in the inner channel determines an effective length of the inner channel;

the plurality of inner channels generate a fan noise cancellation waveform at a frequency based on the effective length of each inner channel; and rotation of the cover relative to the base changes the angular position of the plurality of inner channel baffles in the plurality of inner channels to change the effective length of each inner channel.

9. The chassis of claim 7, further comprising:

a spring in each outer channel of the plurality of outer channels; and a plurality of vanes coupled to the cover, wherein:

airflow in contact with the plurality of vanes causes rotation of the cover relative to the base to change the angular position of the plurality of inner channel baffles in the plurality of inner channels; and the spring is configured to resist rotation of the cover.

10. The chassis of claim 9, wherein one or more of the effective length of each inner channel, the opening in each inner channel, and the spring in each outer channel is configured to cause the plurality of inner channels to generate the fan noise cancellation waveform over a frequency range.

11. The chassis of claim 9, wherein the frequency range corresponds to a frequency associated with a performance drop of a component in the information handling system.

12. The chassis of claim 7, wherein each inner channel comprises a length configured to generate a fan noise cancellation waveform corresponding to a blade passing tone (BPT).

13. A method of manufacturing a fan noise cancellation device, the method comprising:

forming a base comprising a resonance ring for allowing airflow to pass through the fan noise cancellation device;

forming a plurality of inner channels around the resonance ring, wherein each inner channel is formed with a length corresponding to a fan noise cancellation waveform frequency;

forming a plurality of openings on an inner surface of the resonance ring, wherein each inner channel of the plurality of inner channels is in fluid communication with the resonance ring via an opening of the plurality of openings; and coupling a cover to the base, wherein airflow through the resonance ring causes the plurality of inner channels to generate a fan noise cancellation waveform at the fan noise cancellation waveform frequency.

14. The method of manufacturing a fan noise cancellation device of claim 13, wherein forming the plurality of inner channels around the resonance ring comprises forming each inner channel with a length corresponding to a blade passing tone (BPT).

15. The method of manufacturing a fan noise cancellation device of claim 13, wherein:

forming the plurality of inner channels around the resonance ring comprises forming a plurality of inner channel baffles on the cover;

coupling the cover to the base comprises positioning each inner channel baffle in an inner channel of the plurality of inner channels such that an angular position of the inner channel baffle determines an effective length of the inner channel.

16. The method of manufacturing a fan noise cancellation device of claim 15, wherein:

the cover is rotatably coupled to the base; and rotating the cover relative to the base changes the angular position of the inner channel baffle in the inner channel to change the effective length of the inner channel.

17. The method of manufacturing a fan noise cancellation device of claim 16, further comprising:

forming a plurality of outer channels around the plurality of inner channels;

positioning a plurality of springs in the plurality of outer channels;

forming a plurality of outer channel baffles on the cover, wherein each outer channel baffle is configured for contact with a spring of the plurality of springs; and forming a plurality of vanes on the cover to generate a rotation force when in contact with an airflow, wherein coupling the cover to the base comprises:

positioning each inner channel baffle in an inner channel of the plurality of inner channels such that an angular position of the inner channel baffle determines an effective length of the inner channel; and positioning each outer channel baffle in an outer channel of the plurality of outer channels, wherein airflow in contact with the plurality of vanes generates a first rotation force to rotate the cover relative to the base in a first direction to change the angular position of the plurality of inner channel baffles to decrease the effective length of each inner channel of the plurality of inner channels; and contact between the plurality of outer channel baffles with the plurality of springs generates a second rotation force opposite the first rotation force to rotate the cover relative to the base in a second direction to change the angular position of the plurality of inner channel baffles to increase the effective length of each inner channel of the plurality of inner channels.

* * * * *